United States Patent [19]
Saito et al.

[11] Patent Number: 5,332,740
[45] Date of Patent: Jul. 26, 1994

[54] DC-89 DERIVATIVES

[75] Inventors: Hiromitsu Saito, Sagamihara; Satoru Nagamura, Machida; Akira Asai, Fujisawa; Eiji Kobayashi, Numazu; Katsushige Gomi, Susono, all of Japan

[73] Assignee: Kyowa Hakko Kogyo Co., Ltd., Tokyo, Japan

[21] Appl. No.: 46,365

[22] Filed: Apr. 13, 1993

Related U.S. Application Data

[63] Continuation of Ser. No. 732,752, Jul. 19, 1991, abandoned.

[30] Foreign Application Priority Data

Jul. 26, 1990 [JP] Japan .................. 2-198747

[51] Int. Cl.$^5$ .............. A61K 31/435; A61K 31/495; C07D 487/04
[52] U.S. Cl. .................. 514/253; 514/292; 544/126; 544/361; 546/14; 546/84
[58] Field of Search ............... 544/126, 361; 546/14, 546/84; 514/292, 253

[56] References Cited

U.S. PATENT DOCUMENTS 4,923,990  5/1990  Nakano et al. .................. 546/84
5,008,271  4/1991  Kanda et al. .................. 546/84

FOREIGN PATENT DOCUMENTS 354583  2/1990  European Pat. Off. .

*Primary Examiner*—Robert W. Ramsuer
*Attorney, Agent, or Firm*—Fitzpatrick, Cella, Harper & Scinto

[57] ABSTRACT

Novel DC-89 derivatives represented by general formula (I):

wherein X represents Cl or Br; $R^1$ represents hydrogen, $CONR^2R^3$ (in which $R^2$ and $R^3$ independently represent hydrogen, a straight-chain or branched alkyl group having 1 to 4 carbon atoms or phenyl group), (in which n represents an integer of 4 to 7), (in which $R^4$ represents oxygen, N—CH$_3$ or N—CH$_2$CH$_2$NH$_2$), , or $SiR^5R^6R^7$ (in which $R^5$ $R^6$ and $R^7$ independently represent a straight-chain or branched alkyl group having 1 to 4 carbon atoms); and (Abstract continued on next page.)

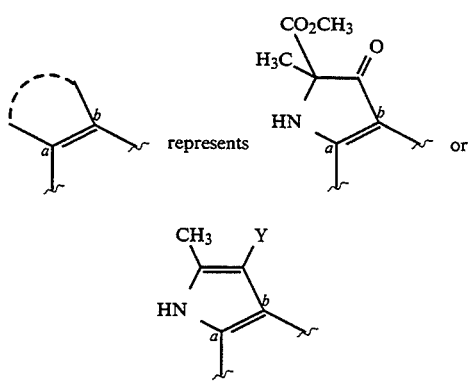 represents 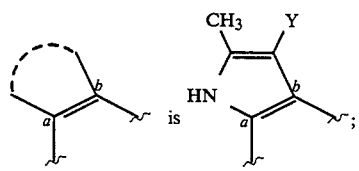 or
(in which Y represents hydrogen or $CO_2CH_3$); provided that when $R^1$ is hydrogen, $CONR^2R^3$ or $SiR^5R^6R^7$,
[structure] is [structure];
and pharmaceutically acceptable salts thereof have an excellent anti-tumor activity and are expected to be useful as anti-tumor compositions.
5 Claims, No Drawings

DC-89 DERIVATIVES

This application is a continuation of application Ser. No. 07/732,752, filed Jul. 19, 1991, now abandoned.

BACKGROUND OF THE INVENTION

The present invention relates to DC-89 derivatives. The compounds have an excellent anti-tumor activity and are expected to be useful as anti-tumor agents.

As compounds similar to the DC-89 derivatives of the present invention, DC-89A1, DC-89A2, DC-89B1 and DC-89B2 represented by the following structural formula are known. These compounds exhibit an antibacterial activity against various bacteria and also show an anti-tumor activity against melanoma B-16, etc.

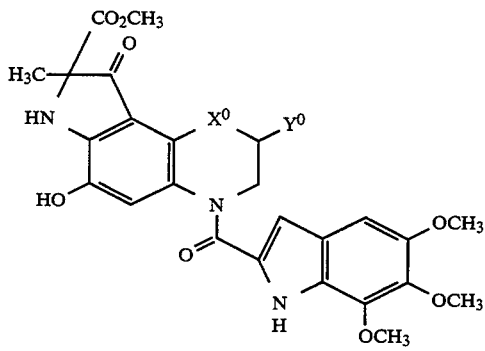

DC-89A1: $X^0 = -CH_2-$, $Y^0 = Cl$
DC-89A2: $X^0 =$ single bond, $Y^0 = CH_2Cl$
DC-89B1: $X^0 = -CH_2-$, $Y^0 = Br$
DC-89B2: $X^0 =$ single bond, $Y^0 = CH_2Br$ DC-89A1 is disclosed in WO 87/06265 (EP-A-0271581); and DC-89A2, DC-89B1 and DC-89B2 are disclosed in Japanese Published Unexamined Patent Application No. 119787/90 (EP-A-0351865) and Japanese Published Unexamined Patent Application No. 139590/89 (EP-A-0318056). Further, DC-88A which has the following structure is disclosed in WO 87/06265 (EP-A-0271581). DC-88A not only shows an antibacterial activity against a variety of bacteria but also exhibits an anti-tumor activity against melanoma B-16, etc.

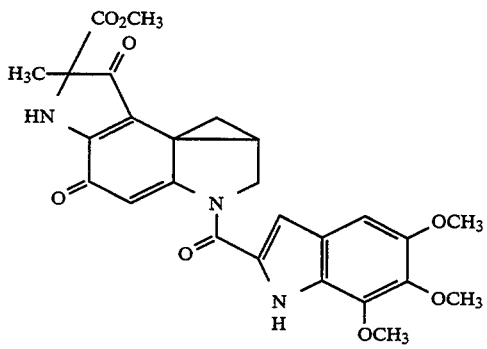

DC-88A derivatives are disclosed in Japanese Published Unexamined Patent Application No. 128379/91 (EP-A-0406749), Japanese Published Unexamined Patent Application No. 288879/90 (EP-A-0354583) and Japanese Published Unexamined Patent Application No. 7287/91 (EP-A-0365041).

Further, as compounds which are structurally similar to the compounds of the present invention, derivatives of SF2582C are disclosed in Japanese Published Unexamined Patent Application No. 275581/89 (EP-A-0339681) and CC-1065 and its derivatives are disclosed in Japanese Published Unexamined Patent Application No. 64695/79 (U.S. Pat. No. 4,169,888), Japanese Published Unexamined Patent Application No. 193989/85 (EP-A-0154445) and WO 88/04659.

SUMMARY OF THE INVENTION

The present invention relates to DC-89 derivatives represented by general formula (I):

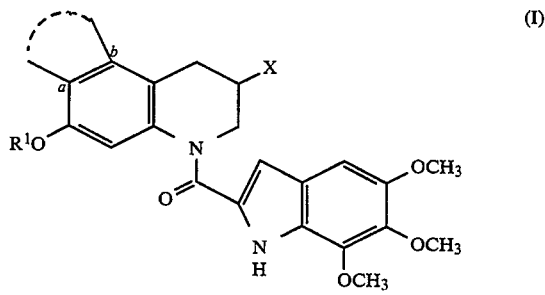

wherein X represents Cl or Br; $R^1$ represents hydrogen, $CONR^2R^3$ (in which $R^2$ and $R^3$ independently represent hydrogen, a straight-chain or branched alkyl group having 1 to 4 carbon atoms, or phenyl group),

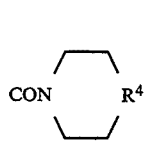

(in which n represents an integer of 4 to 7), $$CON\diagdown\diagup R^4$$

(in which $R^4$ represents oxygen, N—CH$_3$ or N—CH$_2$CH$_2$NH$_2$),

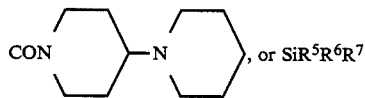, or $SiR^5R^6R^7$ (in which $R^5$, $R^6$ and $R^7$ independently represent a straight-chain or branched alkyl group having 1 to 4 carbon atoms); and (in which Y represents hydrogen or $CO_2CH_3$); provided that when $R^1$ is hydrogen, $CONR^2R^3$ or $SiR^5R^6R^7$,

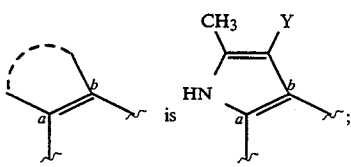

and pharmaceutically acceptable salts thereof.

DETAILED DESCRIPTION OF THE INVENTION

The compounds represented by general formula (I) are hereinafter referred to as Compounds (I). Similarly, the compounds represented by general formulae (II) through (VI) are referred to as Compounds (II) through (VI). Compounds (I-1), (I-2), etc. are intended to be included in Compounds (I) and Compounds (I-2)a, (I-2)b, etc. are intended to be included in Compounds (I-2). In the definition of R in general formula (I), the straight-chain or branched alkyl group having 1 to 4 carbon atoms include, for example, methyl, ethyl, propyl, isopropyl, butyl, isobutyl, sec-butyl and tert-butyl.

As the pharmaceutically acceptable salts of Compounds (I), inorganic acid-addition salts such as hydrochloride, hydrobromide, hydroiodide, sulfate, phosphate and nitrate, and organic acid-addition salts such as acetate, benzoate, maleate, fumarate, succinate, tartrate, citrate, oxalate, glyoxylate, aspartate and methanesulfonate may be mentioned.

The processes for preparing Compounds (I) are described below.

Process 1

Compounds (I-1) [Compounds (I) wherein

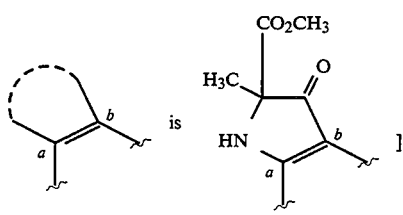

can be prepared according to the following step.

DC-89A1 or DC-89B1 — Step 1 →

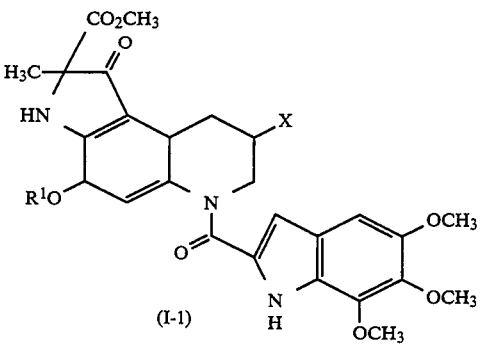

In this formula, X and $R^1$ have the same significances as defined above.

Compound (I-1) can be prepared by allowing DC-89A1 or DC-89B1 obtained by culturing a microorganism belonging to the genus Streptomyces to react with Compound (II) represented by the following formula:

$$R^1-Hal \qquad (II)$$

(wherein Hal represents chlorine, bromine or iodine, and $R^1$ has the same significance as defined above) in an inert solvent in the presence of a base. As the base, imidazole, triethylamine, pyridine, 4-dimethylaminopyridine, etc. may be used. The base is usually used in an amount of 1 to 5 equivalents based on DC-89A1 or DC-89B1, but when the base serves also as a solvent, it is used in large excess of DC-89A1 or DC-89B1. As the inert solvent, pyridine, methylene chloride, dimethylformamide, tetrahydrofuran (THF), toluene, etc. may be used singly or in combination. Compound (II) is usually used in an amount of 1 to 20 equivalents based on DC-89A1 or DC-89B1. The reaction is carried out at $-10°$ C. to $50°$ C. and is completed in 30 minutes to one day.

Process 2

Compounds (I-1) can also be obtained according to the following steps.

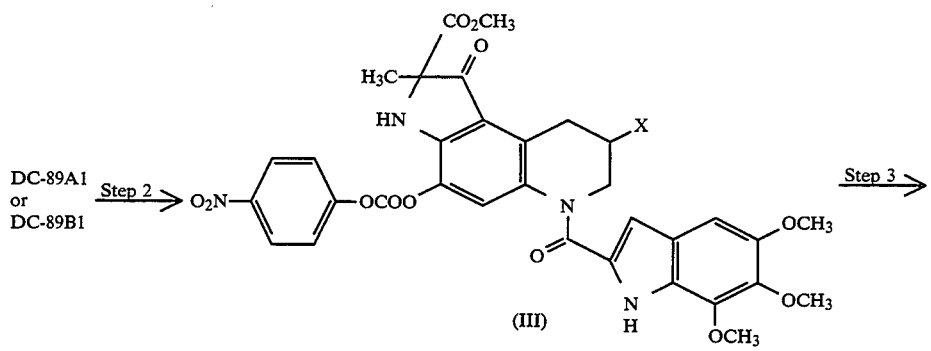

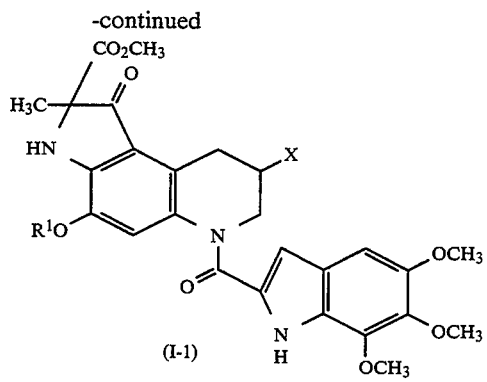

(I-1)

In these formulae, $R^1$ and X have the same significances as defined above.

(Step 2)

Compound (III) can be prepared by allowing DC-89A1 or DC-89B1 to react with p-nitrophenyl chloroformate in an inert solvent in the presence of a base. As the base, triethylamine, pyridine, 4-dimethylaminopyridine, etc. may be used. The base is usually used in an amount of 1 to 5 equivalents based on DC-89A1 or DC-89B1, but when the base serves also as a solvent, it is used in large excess of DC-89A1 or DC-89B1. As the inert solvent, pyridine, methylene chloride, dimethylformamide, THF, toluene, etc. may be used singly or in combination. p-Nitrophenyl chloroformate is usually used in an amount of 1 to 5 equivalents based on DC-89A1 or DC-89B1. The reaction is carried out at $-10°$ C. to 50° C. and is completed in 30 minutes to one day.

(Step 3)

Compound (I-1) can be obtained by allowing Compound (III) to react with Compound (IV) represented by the following formula:

$$R^1-H \qquad (IV)$$

(wherein $R^1$ has the same significance as defined above) in an inert solvent. As the inert solvent, pyridine, methylene chloride, dimethylformamide, THF, toluene, etc. may be used singly or in combination. Compound (IV) is usually used in an amount of 1 to 5 equivalents based on Compound (III). The reaction is carried out at $-10°$ C. to 50° C. and is completed in 30 minutes to one day.

Process 3

Among Compounds (I-2). [Compounds (I) wherein

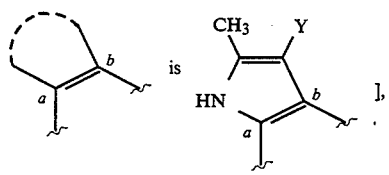

Compounds (I-2)a [Compounds (I-2) wherein $R^1$ is a group other than hydrogen] can be obtained according to the following steps.

Compound (I-1)
or

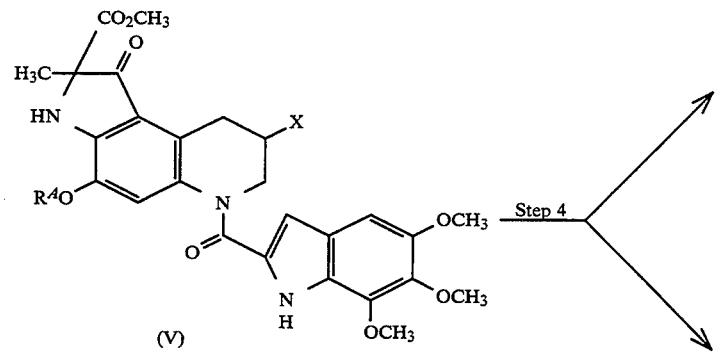

(V)

Step 4

Step 5

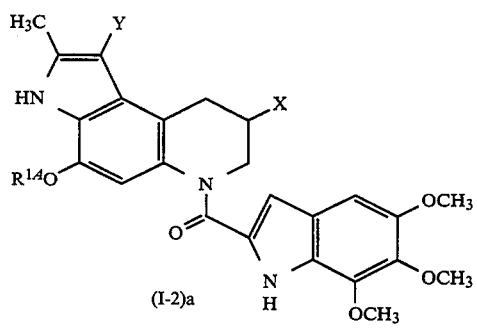

(I-2)a

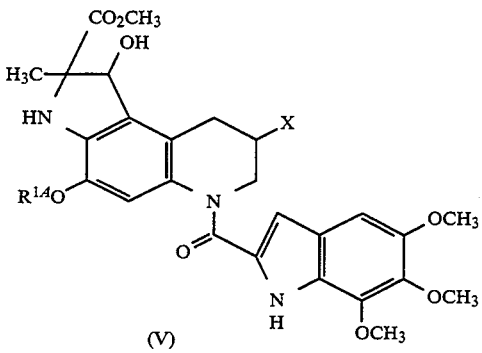

In these formulae, $R^4$ represents $CONR^2R^3$ or $SiR^5R^6R^7$; $R^{1a}$ represents $R^1$ as defined above with the exception of hydrogen; and X, Y, $R^1$, $R^2$, $R^3$, $R^5$, $R^6$ and $R^7$ have the same significances as defined above.

(Step 4)

Compound (I-2)a and Compound (VI) can be prepared by reducing Compound (I-1) or Compound (V) disclosed in EP-A-0365041 in an inert solvent. Examples of the reducing agent include $NaBH_4$, $NaBH_3CN$, $NaAl(OCH_2CH_2OCH_3)_2H_2$ and $AlH[CH_2CH(CH_3)_2]$. The reducing agent is usually used in an amount of 1 to 30 equivalents based on Compound (I-1) or (V). As the inert solvent, water, methanol, ethanol, t-butanol, allyl alcohol, THF, diethyl ether, toluene, etc. are used singly or in combination. The reaction is carried out at −50° C. to 80° C. and is completed in one hour to one day.

(Step 5)

Compound (I-2)a can also be obtained by allowing Compound (VI) with an acid in an inert solvent. As the inert solvent, methylene chloride, chloroform, THF, dioxane, ether, toluene, benzene, etc. are used singly or in combination. Examples of the acid include methanesulfonic acid, p-toluenesulfonic acid, camphor sulfonic acid, sulfuric acid, boron trifluoride-diethyl ether complex, aluminum chloride and zinc chloride, which are usually used in an amount of 0.1 to 3 equivalents based on Compound (VI). The reaction is carried out at 0° C. to 80° C. and is completed in one hour to 15 hours.

Process 4

Compounds (I-2)c [Compounds (I-2) wherein $R^1$ is hydrogen] can be obtained according to the following step.

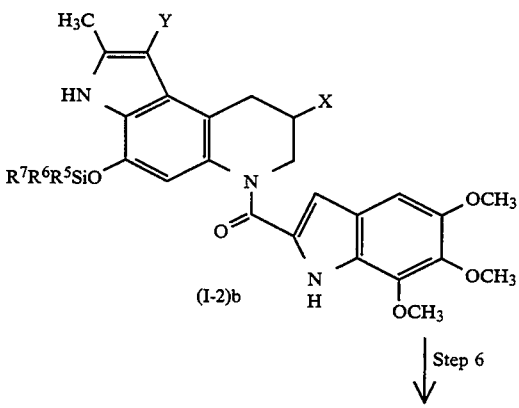

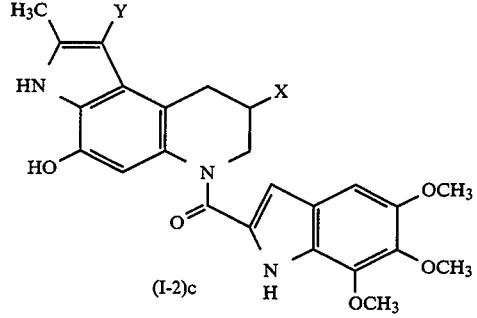

In these formulae, X, Y, $R^5$, $R^6$ and $R^7$ have the same significances as defined above.

(Step 6)

Compound (I-2)c can be prepared by treating Compound (I-2)b [Compound (I-2)a wherein $R^{1a}$ is $SiR^5R^6R^7$] with a fluorine compound such as $(CH_3CH_2CH_2CH_2)_4NF$ or CsF in an inert solvent under acidic conditions. As the inert solvent, methylene chloride, chloroform, THF, acetonitrile, dioxane, toluene, methanol, ethanol, water, etc. may be used singly or in combination. As the acid, hydrochloric acid, hydrobromic acid, phosphoric acid, sulfuric acid, etc. may be used to keep the pH of the reaction solution below 3. The fluorine compound is used in an amount of 1 to 3 equivalents based on Compound (I-2)b. The reaction is carried out at −20° C. to 60° C. and is completed in 1 to 15 hours.

After completion of the reaction in each step, water, an acid or a buffer solution may be added to the reaction mixture, if necessary, followed by extraction with a water-immiscible solvent such as ethyl acetate, chloroform or ether. The extract is washed with water, an aqueous solution of sodium chloride, or the like, and dried over anhydrous sodium sulfate, or the like. Then, the solvent is distilled off, and the residue is subjected to silica gel column chromatography, thin layer chromatography, high performance liquid preparative chromatography, recrystallization, or the like to effect purification.

Intermediates may be directly used in the subsequent reaction without being isolated or purified. Compounds (I) and pharmaceutically acceptable salts thereof may be in the form of adducts with water or various solvents, which are also within the scope of the present invention. Furthermore, all possible stereoisomers of Compounds (I) including optical isomers and mixtures thereof also fall within the scope of the present invention.

The structures and compound numbers of representative compounds which fall under Compounds (I) are shown in Table 1.

The structures and compound numbers of intermediates of the compounds of Table 1 are shown in Table 2.

In Tables 1 and 2, Types A, B and C mean that the compounds fall under Compounds (I-1), (I-2) and (VI), respectively.

TABLE 1

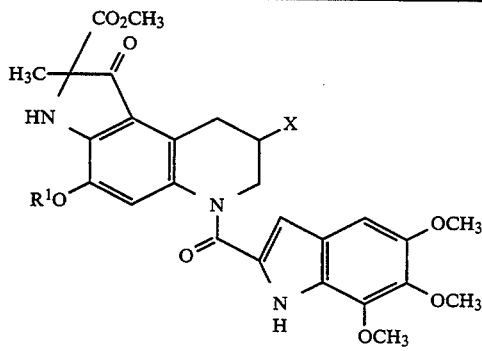

A

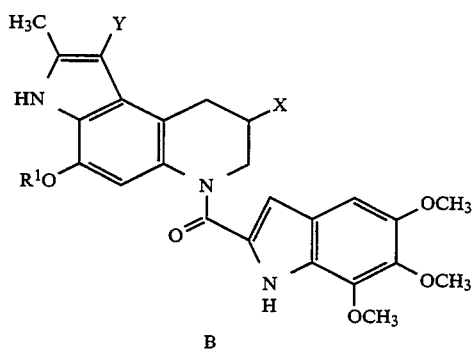

B

| Compound No. | Type | $R^1$ | X | Y |
|---|---|---|---|---|
| 1 | A | CON⌐NCH₃ (piperazine) | Br | — |
| 2 | A | CON⌐NCH₃·HCl (piperazine) | Br | — |
| 3 | A | CON⌐N-CH₂CH₂NH₂ (piperazine) | Br | — |
| 4 | A | CON⌐N-CH₂CH₂NH₂·2HCl (piperazine) | Br | — |
| 5 | A | CON⌐N-piperidinyl | Br | — |

TABLE 1-continued

| 6 | A | CON⌐N-piperidinyl·HCl | Br | — |
| 7 | B | Si(CH₃)₂C(CH₃)₃ | Br | CO₂CH₃ |
| 8 | B | Si(CH₃)₂C(CH₃)₃ | Br | H |
| 9 | B | CON(CH₃)₂ | Br | H |
| 10 | B | Si(CH₃)₂C(CH₃)₃ | Cl | CO₂CH₃ |
| 11 | B | Si(CH₃)₂C(CH₃)₃ | Cl | H |
| 12 | B | CON(CH₃)₂ | Cl | H |
| 13 | A | CON⌐NCH₃ (piperazine) | Cl | — |
| 14 | A | CON⌐NCH₃·HCl (piperazine) | Cl | — |

TABLE 2

(Structure A — same as Table 1 A)

(Structure C — hydroxy ester variant)

| Compound No. | Type | $R^1$ | X |
|---|---|---|---|
| a | A | Si(CH₃)₂C(CH₃)₃ | Br |
| b | A | CON(CH₃)₂ | Br |
| c | C | Si(CH₃)₂C(CH₃)₃ | Br |
| d | A | CON⌐N-CH₂CH₂NHCO₂C(CH₃)₃ | Br |
| e | A | Si(CH₃)₂C(CH₃)₃ | Cl |
| f | C | Si(CH₃)₂C(CH₃)₃ | Cl |
| g | A | CON(CH₃)₂ | Cl |

The pharmacological activity of representative Compounds (I) is shown below.

Therapeutic Effect against Sarcoma 180 Tumor

Five male ddY-strain mice each having a weight of 18 to 20 g were used for each group as test animals, and $5 \times 10^5$ Sarcoma 180 tumor cells were implanted subcutaneously into the animals at the axilla. One day after the implantation, 0.2 ml of physiological saline containing Compound (I) at the concentration indicated in Table 3 was intravenously administered to each mouse. T/C [T: average tumor volume (mm$^3$) of the group treated with the test compound, C: that of the control group which received an intravenous administration of 0.2 ml of physiological saline] was determined seven days after the implantation.

The results are shown in Table 3.

TABLE 3

| Compound No. | Dose (mg/kg) | T/C |
| --- | --- | --- |
| 2 | 2.0 | 0.083 |
| 2 | 1.0 | 0.19 |
| 3 | 1.0 | 0.094 |
| 3 | 0.50 | 0.25 |
| 4 | 1.0 | 0.047 |
| 7 | 2.0 | 0.025 |
| 7 | 1.0 | 0.13 |
| 8 | 2.0 | 0.19 |
| 9 | 0.50 | 0.068 |
| 9 | 0.25 | 0.15 |

Acute Toxicity Test

A test compound was intraperitoneally administered to ddY-strain male mice each weighing 20±1 g. MLD (the minimum lethal dose) was determined by observing the mortality for 14 days after the administration.

The results are shown in Table 4.

TABLE 4

| Compound No. | Acute Toxicity (MLD) mg/kg |
| --- | --- |
| 2 | 5.2 |
| 3 | 2.0 |
| 4 | 2.0 |
| 5 | 2.0 |
| 6 | 4.0 |
| 7 | 4.0 |
| 8 | 8.0 |
| 9 | 0.50 |
| 10 | >8.0 |
| 11 | >8.0 |
| 14 | >16 |

Compounds (I) and pharmaceutically acceptable salts thereof may be used as anti-tumor agents, singly or in combination with at least one pharmaceutically acceptable carrier. For example, Compounds (I) or salts thereof are dissolved in a physiological saline solution or in an aqueous solution of glucose, lactose, mannitol, etc., to prepare a pharmaceutical composition suitable for injection. Alternatively, Compounds (I) or salts thereof are freeze-dried in a conventional manner and mixed with sodium chloride to prepare a powder injection. If necessary, the pharmaceutical composition may contain additives well known in the art of medical preparation, for example, pharmaceutically acceptable salts. Although the dose of the composition may vary depending upon the age, condition, etc. of the patient, it is suitable to administer Compound (I) in an amount of 0.01 to 50 mg/kg/day for mammals including human beings. Administration may be made once a day (single administration or consecutive administrations) or intermittently 1 to 3 times a week or once every 2 to 3 weeks, intravenously. If desired, intraarterial administration, intraperitoneal administration, intrathoracical administration, etc. are also possible in a similar dose and in a similar manner. Further, if desired, the composition may also be administered orally, in a similar dose and in a similar manner. Forms for oral administration include tablets, capsules, powders, granules and ampoules, which contain pharmaceutical auxiliaries well known in the art of medical preparation.

Certain specific embodiments of the present invention are illustrated by the following examples and reference examples.

The physicochemical properties of the compounds shown in the following examples and reference examples were determined with the following equipments.

| NMR | Bruker | AM-400 (400 MHz) |
| --- | --- | --- |
| MS | Hitachi Ltd. | M-80B |
| IR | Nippon Bunko | IR-810 |

As the silica gel, Wakogel C-200 ® manufactured by Wako Pure Chemical Industries Co., Ltd. was used.

In the following examples and reference examples, the expression "conventional treatment" refers to the treatment after the reaction described below.

Citrate or phosphate buffer of pH 5 is added to the reaction mixture, followed by extraction with ethyl acetate or chloroform. The organic solvent layer is washed with a saturated aqueous solution of sodium chloride. After drying over anhydrous sodium sulfate, the solvent is distilled off under reduced pressure.

EXAMPLE 1

Synthesis of Compound 1

Under ice cooling, 47.4 μl (0.34 mmol) of triethylamine and 87.5 mg (0.43 mmol) of p-nitrophenyl chloroformate were added to 14 ml of a solution of 100 mg (0.170 mmol) of DC-89B1 in dichloromethane with stirring. After the mixture was stirred for one hour, 56.6 μl (0.51 mmol) of N-methylpiperazine was added to the mixture, followed by stirring for further one hour. The reaction mixture was subjected to the conventional treatment and the obtained crude product was purified by silica gel column chromatography (50 ml of silica gel, eluting solvent; chloroform:methanol=50:1) to give 96.3 mg (yield 79.3%) of Compound 1.

The physicochemical properties of Compound 1 are as follows.

$^1$H-NMR (CDCl$_3$) δ(ppm); 9.09 (1H, d, J=0.5 Hz), 7.47 (1H, s), 6.78(1H, s), 6.61(1H, d, J=2.3 Hz), 5.44(1H, s), 4.54(1H, m), 4.49(1H, dd, J=6.5, 12.4 Hz), 4.32 (1H, dd, J=1.6, 12.4 Hz) , 4.08 (3H, s), 3.93(3H, s), 3.88(3H, s), 3.86(1H, dd, J=5.9, 19.8 Hz), 3.79(3H, s), 3.71(1H, dd, J=5.3, 19.8 Hz), 3.80–3.60(4H, br), 2.58(4H, br), 2.43 (3H, br), 1.68 (3H, s)

SIMS (m/z); 714, 716(M+1)$^+$

EXAMPLE 2

Synthesis of Compound 2

To 5 ml of a solution of 31.0 mg (0.043 mmol) of Compound 1 in ethanol was added 15 μl (0.087 mmol) of 5.8 N hydrochloric acid-methanol solution, and the mixture was concentrated under reduced pressure. The obtained residue was vacuum-dried to give 32.6 mg (yield 100%) of Compound 2.

The physicochemical properties of Compound 2 are as follows.

$^1$H-NMR (DMSO-d$_6$) δ(ppm); 11.56(1H, d, J=1.8 Hz), 10.74(1H, br), 7.92(1H, s), 7.48(1H, s), 6.89 (1H, s), 6.72(1H, d, J=2.0 Hz), 4.89(1H, m), 4.43 (1H, dd, J=5.1, 13.9 Hz), 4.14(1H, br d, J=13.9 Hz), 3.91(3H, s), 3.79(3H, s), 3.78(3H, s), 3.78(1H, dd, J=5.7, 19.6 Hz), 3.64 (3H, s), 3.51(1H, dd, J=2.8, 19.6 Hz), 3.20 (8H, m), 2.76 (3H, br), 1.50 (3H, s)

EXAMPLE 3

Synthesis of Compound 3

Trifluoroacetic acid (5 ml) was added to 5 ml of a solution of 120 mg (0.142 mmol) of Compound d obtained in Reference Example 4 in dichloromethane, and the mixture was stirred at 25° C. for one hour. The reaction mixture was subjected to the conventional treatment and the obtained crude product was purified by silica gel column chromatography (30 ml of silica gel, eluting solvent; chloroform: methanol=10:1) to give 110 mg (yield 100%) of Compound 3.

The physicochemical properties of Compound 3 are as follows.

$^1$H-NMR (CDCl$_3$) δ(ppm); 11.51 (1H, d, J=1.7 Hz), 8.49 (2H, br), 7.67(2H, s), 6.88(1H, s), 6.70(1H, d, J=1.9 Hz), 4.89(1H, m), 4.44(1H, dd, J=4.5, 13.4 Hz), 4.13(1H, br d, J=13.4 Hz), 3.91(3H, s), 3.79(3H, s), 3.78(3H, s), 3.77(1H, dd, J=5.7, 19.7 Hz), 3.62(3H, s), 3.51(1H, dd, J=3.1, 19.7 Hz), 3.17(2H, m), 3.07(4H, br), 2.58(4H, br), 2.46(2H, br), 1.48(3H, s)
SIMS (m/z); 743, 745(M+1)+

EXAMPLE 4

Synthesis of Compound 4

The same procedure as in Example 2 was repeated except that Compound 3 was used in place of Compound 1, whereby 43.6 mg (yield 99%) of Compound 4 was obtained from mg (0.054 mmol) of Compound 3.

The physicochemical properties of Compound 4 are as follows.

$^1$H-NMR (DMSO-d$_6$) δ(ppm); 11.53(1H, br), 9.26 (2H, br), 7.93(2H, br), 7.36(1H, s), 6.88(1H, s), 6.69(1H, d, J=1.8 Hz), 4.89 (1H, br), 4.42(1H, dd, J=5.1, 13.7 Hz), 4.14(1H, br d, J=13.7 Hz), 3.91(3H, s), 3.79(3H, s), 3.78(3H, s), 3.78(1H, dd, J=5.6, 19.6 Hz), 3.62(3H, s), 3.62(1H, m), 3.52(8H, m), 3.17(4H, m), 1.49(3H, s)

EXAMPLE 5

Synthesis of Compound 5

The same procedure as in Example 1 was repeated except that Compound a was used in place of DC-89B1 and 4-piperidylpiperidine was used in place of N-methylpiperazine, whereby 92.4 mg (yield, 69%) of Compound 5 was obtained from 100 mg (0.17 mmol) of Compound a.

The physicochemical properties of Compound 5 are as follows.

$^1$H-NMR (CDCl$_3$) δ(ppm); 9.09(1H, br), 7.45(1H, s), 6.78(1H, s), 6.60(1H, d, J=2.3 Hz), 5.47(.1H, d, J=9.8 Hz), 4.50(2H, m), 4.32(3H, m), 4.08(3H, s), 3.93(3H, s), 3.87(1H, dd, J=6.0, 19.5 Hz), 3.88(3H, s), 3.79(3H, s), 3.70(1H, dd, J=5.1, 19.5 Hz), 2.97 (1H, br), 2.84(1H, br), 2.64(4H, br), 2.00 (2H, br), 1.75(3H, br), 1.68(3H, br), 1.64(3H, br), 1.52(3H, br)
SIMS (m/z); 782, 784(M+1)+

EXAMPLE 6

Synthesis of Compound 6

The same procedure as in Example 2 was repeated except that Compound 5 was used in place of Compound 1, whereby 33.1 mg (yield 99%) of Compound 6 was obtained from mg (0.041 mmol) of Compound 5.

The physicochemical properties of Compound 6 are as follows.

$^1$H-NMR (DMSO-d$_6$) δ(ppm); 11.55(1H, d, J=1.5 Hz), 9.86(1H, br), 7.81(1H, s), 7.45(1H, s), 6.89(1H, s), 6.72(1H, d, J=2.2Hz), 4.88(1H, br), 4.42(1H, br), 4.32(1H, br), 4.13(2H, br), 3.91(3H, s), 3.79(3H, s), 3.78(3H, s), 3.78(1H, dd, J=5.6, 19.7 Hz), 3.63(3H, s), 3.51(1H, dd, J=2.1, 19.7 Hz), 3.37(3H, br), 2.91(4H, br), 2.10(2H, br), 1.78(7H, m), 1.50(3H, s), 1.40(1H, m)

EXAMPLE 7

Synthesis of Compound 7

In 10 ml of toluene was dissolved 73 mg (0.1 mmol) of Compound c obtained in Reference Example 3, and 48 mg (0.2 mmol) of camphorsulfonic acid was added to the solution, followed by stirring at 50° C. for one hour. A saturated aqueous solution of sodium hydrogencarbonate was added to the obtained reaction mixture, followed by extraction with chloroform. The chloroform layer was washed with a saturated aqueous solution of sodium chloride, dried over anhydrous sodium sulfate, and then concentrated under reduced pressure. The obtained crude product was purified by silica gel column chromatography (40 ml of silica gel, eluting solvent; n-hexane:ethyl acetate=3:1) to give 54 mg (yield 79%) of Compound 7.

The physicochemical properties of Compound 7 are as follows.

$^1$H-NMR (CDCl$_3$) δ(ppm); 9.02(1H, br s), 8.21(1H, br s), 6.55(1H, s), 6.45(1H, d, J=2.3 Hz), 6.05(1H, br s), 4.58(1H, m), 4.24(1H, dd, J=11.0, 5.7 Hz), 4.19(1H, dd, J=10.9, 6.1 Hz), 4.07(1H, br d, J=5.7 Hz), 4.03(3H, s), 3.93(3H, s), 3.90(3H, s), 3.78(3H, s), 3.74(1H, br d, J=6.5 Hz), 2.69(3H, s), 0.88(9H, s), 0.08(6H, s)
IR (KBr) ν(cm$^{-1}$); 3468, 3306, 2936, 2860, 1703, 1615, 1586, 1528, 1496, 1443, 1311, 1256, 1214, 1124, 1088, 997
SIMS (m/z); 688, 686(M+1)+, 606, 454, 452, 234

EXAMPLE 8

Synthesis of Compound 8

In 10 ml of allyl alcohol was dissolved 347 mg (0.49 mmol) of Compound a obtained in Reference Example 1, and 74 mg (1.96 mmol) of sodium borohydride was added to the solution. The mixture was stirred at 0° C. to room temperature for one hour. After 1 N hydrochloric acid was added to the obtained reaction mixture, the mixture was extracted with chloroform. The chloroform layer was washed successively with a saturated aqueous solution of sodium hydrogencarbonate and a saturated aqueous solution of sodium chloride, dried over anhydrous sodium sulfate, and then concentrated under reduced pressure. The obtained crude product was purified by silica gel column chromatography (100 ml of silica gel, eluting solvent; n-hexane:ethyl acetate=2:1) to give 47 mg (yield 15%) of Compound 8.

The physicochemical properties of Compound 8 are as follows.

$^1$H-NMR (CDCl$_3$) δ(ppm); 9.02(1H, br s), 7.88(1H, br s), 6.58(1H, s), 6.36(1H, s), 6.23(1H, d, J=2.3 Hz), 6.18(1H, q, J=0.8 Hz), 4.61(1H, m), 4.24(1H, dd, J=10.7, 5.7 Hz), 4.19(1H, dd, J=10.7, 6.6 Hz), 4.03(3H, s), 3.90(3H, s), 3.80(3H, s), 3.68(1H, dd, J=11.9, 6.4 Hz), 3.41(1H, dd, J=11.9, 6.5 Hz), 2.48(3H, d, J=0.6 Hz), 0.89(9H, s), 0.081(3H, s), 0.085(3H, s)

IR (KBr) ν(cm$^{-1}$); 2932, 2858, 1610, 1596, 1508, 1363, 1313, 1255, 1105, 839

SIMS (m/z); 630, 628 (M+1)$^+$, 628, 234

EXAMPLE 9

Synthesis of Compound 9

In 5 ml of allyl alcohol was dissolved 100 mg (0.151 mmol) of Compound b obtained in Reference Example 2, and 23 mg (0.605 mmol) of sodium borohydride was added to the solution. The mixture was stirred at 0° C. to room temperature for one hour. After 1 N hydrochloric acid was added to the reaction mixture, the mixture was extracted with chloroform. The chloroform layer was washed successively with a saturated aqueous solution of sodium hydrogencarbonate and a saturated aqueous solution of sodium chloride, dried over anhydrous sodium sulfate, and then concentrated under reduced pressure. The obtained crude product was purified by silica gel column chromatography (30 ml of silica gel, eluting solvent; chloroform:acetone =200:1) to give 12 mg (yield 14%) of Compound 9.

The physicochemical properties of Compound 9 are as follows.

$^1$H-NMR (CDCl$_3$) δ(ppm); 9.11(1H, br s), 8.31(1H, br s), 6.86(1H, s), 6.67(1H, s), 6.32(1H, d, J=2.0 Hz), 6.21(1H, q, J=1.1 Hz), 4.59(2H, m), 4.25(1H, dd, J=10.0, 5.3 Hz), 4.05(3H, s), 3.91(3H, s), 3.82(3H, s), 3.71(1H, dd, J=17.5, 6.3 Hz), 3.43(1H, dd, J=17.4, 6.6 Hz), 3.07(3H, s), 2.99(3H, s), 2.46(3H, br s)

IR (KBr) ν(cm$^{-1}$); 3272, 2934, 1711, 1619, 1508, 1490, 1388, 1314, 1169, 750

SIMS (m/z); 587, 585(M+1)$^+$, 507, 234

EXAMPLE 10

Synthesis of Compound 10

In 2 ml of toluene was dissolved 24.4 mg (0.037 mmol) of Compound f obtained in Reference Example 6, and 25.8 mg (0.11 mmol) of camphorsulfonic acid was added to the solution. The mixture was stirred at 50° C. for one hour. A saturated aqueous solution of sodium hydrogencarbonate was added to the reaction mixture, followed by extraction with ethyl acetate. The ethyl acetate layer was washed with a saturated aqueous solution of sodium chloride, dried over anhydrous sodium sulfate, and then concentrated under reduced pressure. The obtained crude product was purified by silica gel column chromatography (20 ml of silica gel, eluting solvent; n-hexane:ethyl acetate=3:1) to give 13.9 mg (yield 58%) of Compound 10.

The physicochemical properties of Compound 10 are as follows.

$^1$H-NMR (CDCl$_3$) δ(ppm); 9.02(1H, br s), 8.20(1H, br s), 6.54(1H, s), 6.45(1H, s), 6.04(1H, d, J=1.9 Hz), 4.56(1H, m), 4.32(1H, br), 4.22(1H, dd, J=11.7, 6.0 Hz), 4.03(3H, s), 3.93(3H, s), 3.90(3H, s), 3.86 (1H, dd, J=17.1, 7.0 Hz), 3.78(3H, s), 3.65(1H, dd, J=17.2, 6.1 Hz), 2.69(3H, s), 0.89(9H, s), −0.07(3H, s), −0.08(3H, s)

IR (KBr) ν(cm$^{-1}$); 2858, 1697, 1615, 1497, 1443, 1313, 1263, 1216, 1125, 1088, 998

EIMS (m/z); 641(M), 408, 371, 234

EXAMPLE 11

Synthesis of Compound 11

In 1 ml of allyl alcohol was dissolved 45 mg (0.068 mmol) of Compound e obtained in Reference Example 5, and 7.7 mg (0.20 mmol) of sodium borohydride was added to the solution. The mixture was stirred at 0° C. to room temperature for one hour. After 0.5 N hydrochloric acid was added to the reaction mixture, the mixture was extracted with chloroform. The chloroform layer was washed successively with a saturated aqueous solution of sodium hydrogencarbonate and a saturated aqueous solution of sodium chloride, dried over anhydrous sodium sulfate, and then concentrated under reduced pressure. The obtained crude product was purified by silica gel column chromatography (30 ml of silica gel, eluting solvent; n-hexane:ethyl acetate=3:1) to give 3.4 mg (yield 9%) of Compound 11.

The physicochemical properties of Compound 11 are as follows.

$^1$H-NMR (CDCl$_3$) δ(ppm); 8.99(1H, br s), 7.87(1H, br s), 6.58(1H, s), 6.37(1H, s), 6.22(1H, d, J=1.9 Hz), 6.19 (1H, dq, J=2.1, 0.8 Hz), 4.57 (1H, m), 4.38 (1H, dd, J=12.4, 2.8 Hz), 4.21 (1H, dd, J=12.5, 5.2 Hz), 4.03(3H, s), 3.90(3H, s), 3.80(3H, s), 3.56(1H, dd, J=17.2, 6.4 Hz), 3.25(1H, dd, J=17.2, 6.1 Hz), 2.49(3H, br s), 0.90(9H, s), −0.07(3H, s), −0.08(3H, s)

IR (KBr) ν(cm1); 2932, 1620, 1507, 1363, 1314, 1261, 1105, 835

EIMS (m/z); 583(M)$^+$, 350, 313 234

EXAMPLE 12

Synthesis of Compound 12

In 5 ml of allyl alcohol was dissolved 81.7 mg (0.133 mmol) of Compound g obtained in Reference Example 7, and 15.1 mg (0.40 mmol) of sodium borohydride was added to the solution. The mixture was stirred at 0° C. to room temperature for one hour. After 1 N hydrochloric acid was added to the reaction mixture, the mixture was extracted with ethyl acetate. The ethyl acetate layer was washed successively with a saturated aqueous solution of sodium hydrogencarbonate and a saturated aqueous solution of sodium chloride, dried over anhydrous sodium sulfate, and then concentrated under reduced pressure. The obtained crude product was purified by silica gel column chromatography (20 ml of silica gel, eluting solvent; chloroform:methanol =100:1) to give 10.6 mg (yield 15%) of Compound 12.

The physicochemical properties of Compound 12 are as follows.

$^1$H-NMR (CDCl$_3$) δ(ppm); 9.10(1H, br s), 8.29(1H, br s), 6.87(1H, s), 6.67(1H, s), 6.31(1H, d, J=2.0 Hz), 6.22(1H, br s), 4.55(1H, m), 4.47(1H, br d, J=12.5 Hz), 4.21(1H, dd, J=12.5, 6.8 Hz), 4.05(3H, s), 3.91(3H, s), 3.82(3H, s), 3.58(1H, dd, J=17.3, 6.5 Hz), 3.27(1H, dd, J=17.3, 6.3 Hz), 3.07 (3H, s), 2.99(3H, s), 2.47(3H, br s)

IR (KBr) $\nu(\text{cm}^{-1})$; 2934, 1711, 1620, 1507, 1491, 1389, 1316, 1223, 1175, 997

EIMS (m/z); 540(M)+, 307, 270, 234

EXAMPLE 13

Synthesis of Compound 13

The same procedure as in Example 1 was repeated except that DC-89A1 was used in place of DC-89B1, whereby mg (yield 73%) of Compound 13 was obtained from 100 mg (0.184 mmol) of DC-89A1.

The physicochemical properties of Compound 13 are as follows.

$^1$H-NMR (DMSO-d$_6$) δ(ppm); 11.54(1H, d, J=1.5 Hz), 7.80(1H, s), 7.40(1H, s), 6.88(1H, s), 6.71(1H, d, J=2.0 Hz), 4.78(1H, m), 4.39(1H, dd, J=4.7, 13.5 Hz), 4.07(1H, dd, J=1.9, 13.5 Hz), 3.91(3H, s), 3.79(3H, s), 3.78(3H, s), 3.64(3H, s), 3.60(1H, dd, J=5.6, 19.4 Hz), 3.35(1H, dd, J=2.8, 19.4 Hz), 3.19–3.44(8H, m), 2.32(3H, br), 1.49(3H, s)

SIMS (m/z); 670(M+1)+

EXAMPLE 14

Synthesis of Compound 14

The same procedure as in Example 2 was repeated except that Compound 13 was used in place of Compound 1, whereby 40 mg (yield 95%) of Compound 14 was obtained from 40 mg of Compound 13.

The physicochemical properties of Compound 14 are as follows.

$^1$H-NMR (DMSO-d$_6$) δ(ppm); 11.54(1H, d, J=1.6 Hz), 10.47(1H, br), 7.88(1H, br), 7.47(1H, s), 6.89(1H, s), 6.71(1H, d, J=1.8 Hz), 4.78(1H, m), 4.40(1H, br d, J=10.8 Hz), 4.08(1H, br d, J=13.1 Hz), 3.91(3H, s), 3.79(3H, s), 3.78(3H, s), 3.64(3H, s), 3.60(1H, dd, J=5.9, 19.7 Hz), 3.38(1H, dd, J=2.5, 19.7 Hz), 3.10–3.46(8H, m), 2.80(3H, br), 1.51(3H, s)

REFERENCE EXAMPLE 1

Synthesis of Compound a

In 5 ml of N,N-dimethylformamide was dissolved 100 mg (0.17 mmol) of DC-89B1, and 40.5 mg (0.56 mmol) of imidazole and 90 mg (0.56 mmol) of t-butyldimethylsilyl chloride were added to the solution at 0° C. The mixture was stirred at 0° C. for 3 hours. After 1N hydrochloric acid was added to the reaction mixture, the mixture was extracted with ethyl acetate. The ethyl acetate layer was washed successively with a saturated aqueous solution of sodium hydrogencarbonate and a saturated aqueous solution of sodium chloride, dried over anhydrous sodium sulfate, and then concentrated under reduced pressure. The obtained crude product was purified by silica gel column chromatography (30 ml of silica gel, eluting solvent; n-hexane:ethyl acetate=3:1) to give 122 mg (yield 99%) of Compound a.

The physicochemical properties of Compound a are as follows.

$^1$H-NMR (CDCl$_3$) δ(ppm); 9.03(1H, d, J=0.7 Hz), 6.90 (1H, s), 6.72(1H, s), 6.52(1H, d, J=2.2 Hz), 5.02(1H, s), 4.57(1H, m), 4.46(1H, dd, J=13.3, 6.2 Hz), 4.20(1H, br d, J=13.3 Hz), 4.06(3H, s), 3.92(3H, s), 3.85(3H, s), 3.83(1H, dd, J=19.3, 6.2 Hz), 3.78(3H, s), 3.65(1H, dd, J=19.3, 5.2 Hz), 1.69(3H, s), 0.91(9H, S), 0.15(6H, s)

IR (KBr) $\nu(\text{cm}^{-1})$; 2936, 2860, 1747, 1701, 1612, 1508, 1394, 1301, 1254, 1109, 828

SIMS (m/z); 704, 702(M+1)+, 622, 470, 468, 387, 329, 234

REFERENCE EXAMPLE 2

Synthesis of Compound b

In 2.5 ml of pyridine was dissolved 50 mg (0.085 mmol) of DC-89B1, and 0.078 ml (0.85 mmol) of N,N-dimethylcarbamoyl chloride was added to the solution at 0° C. The mixture was stirred at 0° C. to room temperature for 4 hours. After 1N hydrochloric acid was added to the reaction mixture, the mixture was extracted with chloroform. The chloroform layer was washed successively with a saturated aqueous solution of sodium hydrogencarbonate and a saturated aqueous solution of sodium chloride, dried over anhydrous sodium sulfate, and then concentrated under reduced pressure. The obtained crude product was purified by silica gel column chromatography (30 ml of silica gel, eluting solvent; n-hexane:ethyl acetate=2:3) to give 55 mg (yield 98%) of Compound b.

The physicochemical properties of Compound b are as follows.

$^1$H-NMR (CDCl$_3$) δ(ppm); 9.09 (1H, br s), 7.46(1H, s), 6.78(1H, s), 6.60(1H, d, J=2.3 Hz), 5.46(1H, s), 4.55(1H, m), 4.48(1H, dd, J=12.8, 6.4 Hz), 4.32(1H, dd, J=12.8, 2.6 Hz), 4.08(3H, s), 3.93(3H, s), 3.88(3H, s), 3.88(1H, dd, J=19.4, 6.0 Hz), 3.79(3H, s), 3.71(1H, dd, J=19.4, 5.3 Hz), 3.07(3H, s), 3.00(3H, s), 1.68(3H, s)

IR (KBr) $\nu(\text{cm}^{-1})$; 3332, 2938, 1715, 1623, 1506, 1388, 1312, 1245, 1161

SIMS (m/z); 661, 659(M+1)+, 579, 427, 425, 344, 234

REFERENCE EXAMPLE 3

Synthesis of Compound c

In 10 ml of allyl alcohol was dissolved 347 mg (0.49 mmol) of Compound a obtained in Reference Example 1, and 74 mg (1.96 mmol) of sodium borohydride was added to the solution. The mixture was stirred at 0° C. to room temperature for one hour. After 1N hydrochloric acid was added to the reaction mixture, the mixture was extracted with chloroform. The chloroform layer was washed successively with a saturated aqueous solution of sodium hydrogencarbonate and a saturated aqueous solution of sodium chloride, dried over anhydrous sodium sulfate, and then concentrated under reduced pressure. The obtained crude product was purified by silica gel column chromatography (100 ml of silica gel, eluting solvent; n-hexane:ethyl acetate=1:1) to give 73 mg (yield 21%) of Compound c.

The physicochemical properties of Compound c are as follows.

$^1$H-NMR (CDCl$_3$) δ(ppm); 9.00(1H, br s), 6.67(1H, s), 6.63(1H, s), 6.35(1H, d, J=2.1 Hz), 5.34(1H, d, J=9.3 Hz), 4.52(3H, m), 4.16(1H, dd, J=13.9, 6.7 Hz), 4.05(3H, s), 3.91(3H, s), 3.84(3H, s), 3.76(3H, s), 3.44(1H, br d, J=2.9 Hz), 3.42(1H, br d, J=3.4 Hz), 1.74(1H, d, J=9.4 Hz), 1.61(3H, s), 0.89(9H, s), 0.51(3H, s), 0.23(3H, s)

IR (KBr) $\nu(\text{cm}^{-1})$; 2934, 2858, 1734, 1616, 1495, 1389, 1255, 1108, 1047, 838

SIMS (m/z); 706, 704(M+1)+, 626, 472, 470, 391, 234

REFERENCE EXAMPLE 4

Synthesis of Compound d

The same procedure as in Example 1 was repeated except that N-tert-butoxycarbonylaminoethylpiperazine was used in place of N-methylpiperazine, whereby 218 mg (yield 79% of Compound d was obtained from 200 mg of DC-89B1.

The physicochemical properties of Compound d are as follows.

$^1$H-NMR (CDCl$_3$) δ(ppm); 9.14(1H, br), 7.45(1H, s), 6.74(1H, s), 6.56(1H, d, J=2.2 Hz), 5.60(1H, br), 4.50(2H, m), 4.29(1H, m), 4.07(3H, s), 3.93(3H, s), 3.88(3H, s), 3.86(1H, dd, J=5.9, 19.4 Hz), 3.77(3H, s), 3.70(1H, dd, J=6.7, 19.4 Hz), 3.49(6H, m), 2.50(6H, m), 1.68(3H, s), 1.45(9H, s)
SIMS (m/z); 843, 845(M+1)+

REFERENCE EXAMPLE 5

Synthesis of Compound e

In 1 ml of N,N-dimethylformamide was dissolved 50 mg (0.092 mmol) of DC-89A1, and 19.4 mg (0.28 mmol) of imidazole and 41.6 mg (0.28 mmol) of t-butyldimethylsilyl chloride were added to the solution at 0° C. The mixture was stirred at 0° C. for 3 hours. After 1N hydrochloric acid was added to the reaction mixture, the mixture was extracted with ethyl acetate- The ethyl acetate layer was washed successively with a saturated aqueous solution of sodium hydrogencarbonate and a saturated aqueous solution of sodium chloride, dried over anhydrous sodium sulfate, and then concentrated under reduced pressure. The obtained crude product was purified by silica gel column chromatography (20 ml of silica gel, eluting solvent; n-hexane:ethyl acetate=3:1) to give 50.8 mg (yield 84%) of Compound e.

The physicochemical properties of Compound e are as follows.

$^1$H-NMR (CDCl$_3$) δ(ppm); 9.03(1H, br s), 6.90(1H, s), 6.71(1H, s), 6.50(1H, d, J=2.1 Hz), 5.02(1H, br), 4.52(1H, m), 4.44(1H, dd, J=13.0, 5.9 Hz), 4.12 (1H, br d, J=13.1 Hz), 4.06(3H, s), 3.92(3H, s), 3.86(3H, s), 3.79(3H, s), 3.68(1H, dd, J=19.1, 6.1 Hz), 3.51(1H, dd, J=19.1, 4.6 Hz), 1.69(3H, s), 0.91(9H, s), 0.17(6H, s)
IR (KBr) ν(cm$^{-1}$); 2860, 1749, 1701, 1612, 1510, 1394, 1300, 1260, 1108, 828
EIMS (m/z); 657(M)+, 621, 424, 388, 329, 234

REFERENCE EXAMPLE 6

Synthesis of Compound f

In 1 ml of allyl alcohol was dissolved 45 mg (0.068 mmol) of Compound e obtained in Reference Example 5, and 7.7 mg (0.20 mmol) of sodium borohydride was added to the solution. The mixture was stirred at 0° C. to room temperature for one hour. After 0.5N hydrochloric acid was added to the reaction mixture, the mixture was extracted with chloroform. The chloroform layer was washed successively with a saturated aqueous solution of sodium hydrogencarbonate and a saturated aqueous solution of sodium chloride, dried over anhydrous sodium sulfate, and then concentrated under reduced pressure. The obtained crude product was purified by silica gel column-chromatography (30 ml of silica gel, eluting solvent; n-hexane:ethyl acetate=2:1) to give 18 mg (yield 40%) of Compound f.

The physicochemical properties of Compound f are as follows.

$^1$H-NMR (CDCl$_3$) δ(ppm); 9.01(1H, br s), 6.68(1H, s), 6.67(1H, s), 6.37(1H, d, J=1.8 Hz), 5.34(1H, s), 4.56(1H, br), 4.49(1H, ml, 4.41(1H, dd, J=12.9, 3.5 Hz), 4.11(1H, dd, J=12.8, 6.7 Hz), 4.05(3H, s), 3.91(3H, s), 3.85(3H, s), 3.77(3H, s), 3.32(1H, br d, J=5.9 Hz), 3.30(1H, br d, J=6.2 Hz), 1.75 (1H, br), 1.66(3H, s), 0.89(9H, s), −0.012(3H, s), −0.03(3H, s)
IR (KBr) ν(cm$^{-1}$); 2934, 2858, 1733, 1617, 1496, 1389, 1312, 1220, 1121, 838
EIMS (m/z); 659(M)+, 426, 234

REFERENCE EXAMPLE 7

Synthesis of Compound g

In 5 ml of pyridine was dissolved 100 mg (0.184 mmol) of DC-89A1, and 0.254 ml (2.76 mmol) of N,N-dimethylcarbamoyl chloride was added to the solution at 0° C. The mixture was stirred at 0° C. to room temperature for 3 hours. After 1N hydrochloric acid was added to the reaction mixture, the mixture was extracted with chloroform. The chloroform layer was washed successively with a saturated aqueous solution of sodium hydrogencarbonate and a saturated aqueous solution of sodium chloride, dried over anhydrous sodium sulfate, and then concentrated under reduced pressure. The obtained crude product was purified by silica gel column chromatography (40 ml of silica gel, eluting solvent; chloroform:methanol=100:1) to give 111.8 mg (yield 98%1 of Compound g.

The physicochemical properties of Compound g are as follows.

$^1$H-NMR (CDCl$_3$) δ (ppm); 9.07 (1H, br s), 7.46(1H, s), 6.78(1H, s), 6.59(1H, d, J=2.3 Hz), 5.40(1H, s), 4.50(2H, m), 4.23(1H, br d, J=10.7 Hz), 4.08(3H, s), 3.93(3H, s), 3.88(3H, s), 3.79(3H, s), 3.72(1H, dd, J=19.3, 5.8 Hz), 3.57(1H, dd, J=19.2, 5.0 Hz), 3.07(3H, s), 3.00(3H, s), 1.69(3H, s)
IR (KBr) ν(cm$^{-1}$); 3268, 2938, 1739, 1618, 1509, 1387, 1259, 1224, 1164, 1110, 996
EIMS (m/z); 614(M)+, 578, 381, 345, 234

What is claimed is:

1. A DC-89 derivative represented by general formula (I):

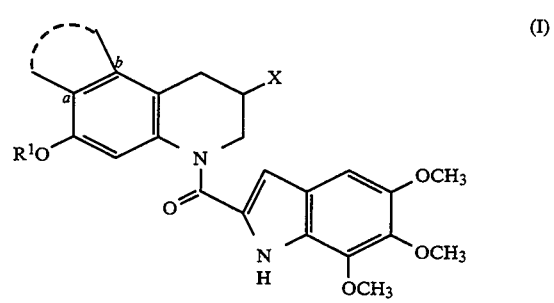

wherein X represents Cl or Br; R$^1$ represents

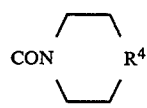

(in which R⁴ represents oxygen, N—CH₃ or N—CH₂CH₂NH₂), or;

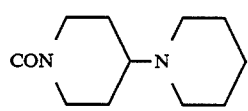

and

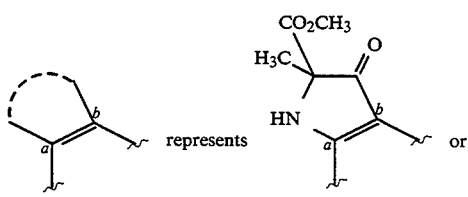 or

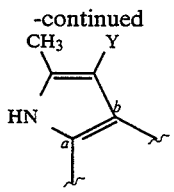

(in which Y represents hydrogen or CO₂CH₃); or a pharmaceutically acceptable salt thereof.

2. A compound according to claim 1, wherein

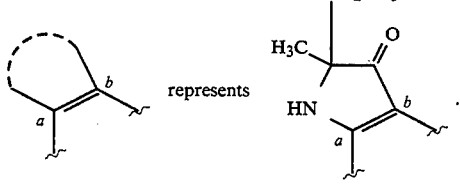

3. A compound according to claim 2, wherein R¹ represents

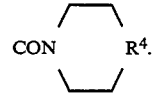

4. A compound according to claim 3, wherein R⁴ represents N—CH₃.

5. A pharmaceutical composition comprising a pharmaceutical carrier and, as an active ingredient, an effective amount of the DC-89 derivative as defined by claim 1.

* * * * *

UNITED STATES PATENT AND TRADEMARK OFFICE
CERTIFICATE OF CORRECTION

PATENT NO. : 5,332,740
DATED : July 26, 1994
INVENTOR(S) : HIROMITSU SAITO, ET AL.

It is certified that error appears in the above-identified patent and that said Letters Patent is hereby corrected as shown below:

COLUMN 1

Line 68, "lar-to" should read --lar to--.

COLUMN 8

Line 15, "(V)" should read --(VI)--.

COLUMN 13

Line 41, "from mg" should read --from 40 mg--.

COLUMN 14

Line 10, "from mg" should read --from 32 mg--.
Line 46, "6.1 Hz);" should read --6.1 Hz),--.

COLUMN 16

Line 10, "641(M)," should read --641(M)$^+$,--.
Line 40, "v(cm1);" should read --v(cm$^{-1}$);--.

COLUMN 17

Line 13, "whereby mg" should read --whereby 90 mg--.

COLUMN 18

Line 17, "chloroform-" should read --chloroform.--.

UNITED STATES PATENT AND TRADEMARK OFFICE
CERTIFICATE OF CORRECTION

PATENT NO. : 5,332,740
DATED : July 26, 1994
INVENTOR(S) : HIROMITSU SAITO, ET AL.

It is certified that error appears in the above-identified patent and that said Letters Patent is hereby corrected as shown below:

COLUMN 19

Line 8, "(yield 79% of" should read --(yield 79%) of--.
    Line 30, "ethyl acetate-" should read --ethyl acetate.--.

COLUMN 20

Line 9, "4.49(1H, ml," should read --4.49(1H, m),--.
    LIne 37, "(yield 98%1" should read --(yield 98%)--.

COLUMN 21

Line 13, "or;" should read --or--.

Signed and Sealed this

Fifteenth Day of November, 1994

Attest:

BRUCE LEHMAN

*Attesting Officer*    *Commissioner of Patents and Trademarks*